(12) United States Patent
Hoefer et al.

(10) Patent No.: US 7,750,100 B2
(45) Date of Patent: Jul. 6, 2010

(54) CATALYTIC PROCESS FOR PREPARING (METH)ACRYLATES FROM N-HYDROXYALKYLATED LACTAMS

(75) Inventors: Frank Hoefer, Bad Duerkheim (DE); Hermann Bergmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 861 days.

(21) Appl. No.: 11/553,755

(22) Filed: Oct. 27, 2006

(65) Prior Publication Data

US 2007/0123673 A1    May 31, 2007

(30) Foreign Application Priority Data

Nov. 3, 2005    (DE) .................. 10 2005 052 931

(51) Int. Cl.
*C08F 18/00* (2006.01)
*C08F 26/08* (2006.01)
(52) U.S. Cl. .................. 526/264; 526/301; 526/310; 526/311; 526/312; 526/314; 526/319; 526/320
(58) Field of Classification Search .................. 526/173, 526/176, 179, 181, 264, 301, 320, 310, 311, 526/312, 314, 319
See application file for complete search history.

(56) References Cited

U.S. PATENT DOCUMENTS

| 2,882,262 | A | * | 4/1959 | Smith et al. .................. 526/264 |
| 3,067,163 | A | | 12/1962 | Bauer |
| 3,342,786 | A | | 9/1967 | Emmons |
| 3,371,040 | A | | 2/1968 | Emmons |
| 3,386,998 | A | | 6/1968 | Emmons |

FOREIGN PATENT DOCUMENTS

| GB | 930668 | 7/1963 |
| NL | 6506333 | 11/1965 |
| WO | WO 03/006568 A1 | 1/2003 |

OTHER PUBLICATIONS

U.S. Appl. No. 12,524,587, filed Jul. 27, 2009, Bergmann, et al.
U.S. Appl. No. 12,525,686, filed Aug. 4, 2009, Bergmann, et al.
U.S. Appl. No. 12/525,826, filed Aug. 5, 2009, Bergmann, et al.

* cited by examiner

*Primary Examiner*—David Wu
*Assistant Examiner*—Marie Reddick
(74) *Attorney, Agent, or Firm*—Oblon, Spivak, McClelland, Maier & Neustadt, L.L.P.

(57) ABSTRACT

Process for catalytically preparing (meth)acrylates of N-hydroxyalkylated lactams, and use thereof.

16 Claims, No Drawings

CATALYTIC PROCESS FOR PREPARING (METH)ACRYLATES FROM N-HYDROXYALKYLATED LACTAMS

The present invention relates to a process for catalytically preparing (meth)acrylates of N-hydroxyalkylated lactams and to their use.

(Meth)acrylic esters are prepared usually by catalytically esterifying (meth)acrylic acid or transesterifying other (meth) acrylic esters with alcohols in the presence of strong acids or strong bases. Acid- or base-sensitive (meth)acrylic esters therefore generally cannot be prepared selectively by an esterification or transesterification.

WO 03/6568 describes the acidic esterification of acrylic acid with hydroxyethylpyrrolidone with only 71% yield.

NL 6506333 and GB 930668 disclose the transesterification of N-hydroxyalkyllactams with (meth)acrylic esters in the presence of alkali metal or ammonium alkoxides, and also titanium tetraalkoxides.

A disadvantage of these processes is that the metal compounds are moisture-sensitive and are therefore deactivated readily. In addition, traces of the catalysts remaining in the product influence any subsequent polymerization, and therefore have to be removed from the product in a complicated manner. Such a removal is usually carried out by means of an aqueous scrubbing, so that the product subsequently has to be dried.

GB 930668 additionally discloses the preparation of lactam (meth)acrylates by reacting N-hydroxyalkyllactams with (meth)acryloyl chloride.

The use of (meth)acryloyl chloride in the reactions described leads to salt formation and, owing to its high reactivity, to unselective reactions, for example Michael additions.

It was an object of the present invention to provide a further process with which (meth)acrylates are preparable from N-hydroxyalkylated lactams in high conversions and high purities from simple reactants. The synthesis should lead to products with low color number and high purity. In particular, the fraction of Michael adducts should be suppressed. Any catalyst needed should also be simple to remove and not result in any further aftertreatments, for example in the form of workup steps, of the reaction product.

The object is achieved by a process for preparing (meth) acrylates of N-hydroxy-alkylated lactams, in which cyclic N-hydroxyalkylated lactams (C)

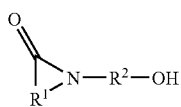

(C)

in which $R^1$ is $C_1$-$C_5$-alkylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO) O—, —O(CO)(NH)—, —O(CO)— or —(CO)O— groups, where the radicals mentioned may each be substituted by aryl, alkyl, aryloxy, alkyloxy, heteroatoms and/or heterocycles, with the proviso that $R^1$ must not have any atom other than a carbon atom directly adjacent to the lactam carbonyl group, $R^2$ is $C_1$-$C_{20}$-alkylene, $C_5$-$C_{12}$-cycloalkylene, or $C_6$-$C_{12}$-arylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, or $R^2$—OH is a group of the formula —$[X_i]_k$—H, k is from 1 to 50 and $X_i$, for each i=1 to k, may independently be selected from the group of —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O—, —CH($CH_3$)—$CH_2$—O—, —$CH_2$—C($CH_3$)$_2$—C—, —C($CH_3$)$_2$—$CH_2$—O—, —$CH_2$—$CH_2$—$CH_2$—C—, —$CH_2$—$CH_2$—$CH_2$—$CH_2$—C—, —$CH_2$—CHVin-O—, —CHVin-$CH_2$—O—, —$CH_2$—CHPh-O— and —CHPh-$CH_2$—O—, where Ph is phenyl and Vin is vinyl, in the presence of at least one heterogeneous inorganic salt (S) are esterified with (meth)acrylic acid or transesterified with at least one (meth)acrylic ester (D).

With the aid of the process according to the invention, it is possible to prepare (meth)acrylates of N-hydroxyalkylated lactams with at least one of the following advantages:

high yield,
good color numbers and
no washing steps required for the purification of the reaction mixture.

In this document, (meth)acrylic acid represents methacrylic acid and acrylic acid, preferably methacrylic acid.

In the above definitions, $C_1$-$C_{20}$-alkylene optionally substituted by aryl, alkyl, aryloxy, alkyloxy, heteroatoms and/or heterocycles means, for example, methylene, 1,2-ethylene, 1,2-propylene, 1,3-propylene, 1,4-butylene, 1,6-hexylene, 2-methyl-1,3-propylene, 2-ethyl-1,3-propylene, 2,2-dimethyl-1,3-propylene, 2,2-dimethyl-1,4-butylene, $C_5$-$C_{12}$-cycloalkylene optionally substituted by aryl, alkyl, aryloxy, alkyloxy, heteroatoms and/or heterocycles means, for example, cyclopropylene, cyclopentylene, cyclohexylene, cyclooctylene, cyclododecylene, $C_1$-$C_{20}$-alkylene optionally substituted by aryl, alkyl, aryloxy, alkyloxy, heteroatoms and/or heterocycles and interrupted by one or more oxygen and/or sulfur atoms and/or one or more substituted or unsubstituted imino groups and/or by one or more cycloalkyl, —(CO)—, —O(CO)O—, —(NH) (CO)O—, —O(CO)(NH)—, —O(CO)— or —(CO)O— groups means, for example, 1-oxa-1,3-propylene, 1,4-dioxa-1,6-hexylene, 1,4,7-trioxa-1,9-nonylene, 1-oxa-1,4-butylene, 1,5-dioxa-1,8-octylene, 1-oxa-1,5-pentylene, 1-oxa-1,7-heptylene, 1,6-dioxa-1,10-decylene, 1-oxa-3-methyl-1,3-propylene, 1-oxa-3-methyl-1,4-butylene, 1-oxa-3,3-dimethyl-1,4-butylene, 1-oxa-3,3-dimethyl-1,5-pentylene, 1,4-dioxa-3,6-dimethyl-1,6-hexylene, 1-oxa-2-methyl-1,3-propylene, 1,4-dioxa-2,5-dimethyl-1,6-hexylene, 1-oxa-1,5-pent-3-enylene, 1-oxa-1,5-pent-3-ynylene, 1,1-, 1,2-, 1,3- or 1,4-cyclohexylene, 1,2- or 1,3-cyclopentylene, 1,2-, 1,3- or 1,4-phenylene, 4,4'-biphenylene, 1,4-diaza-1,4-butylene, 1-aza-1,3-propylene, 1,4,7-triaza-1,7-heptylene, 1,4-diaza-1,6-hexylene, 1,4-diaza-7-oxa-1,7-heptylene, 4,7-diaza-1-oxa-1,7-heptylene, 4-aza-1-oxa-1,6-hexylene, 1-aza-4-oxa-1,4-butylene, 1-aza-1,3-propylene, 4-aza-1-oxa-1,4-butylene, 4-aza-1,7-dioxa-1,7-heptylene, 4-aza-1-oxa-4-methyl-1,6-hexylene, 4-aza-1,7-dioxa-4-methyl-1,7-heptylene, 4-aza-1,7-dioxa-4-(2'-hydroxyethyl)-1,7-heptylene, 4-aza-1-oxa-(2'-hydroxyethyl)-1,6-hexylene or 1,4-piperazinylene and $C_6$-$C_{12}$-arylene optionally substituted by aryl, alkyl, aryloxy, alkyloxy, heteroatoms and/or heterocycles means, for example, 1,2-, 1,3- or 1,4-phenylene, 4,4'-biphenylene, tolylene or xylylene.

Examples of $R^1$ are 1,2-ethylene, 1,2-propylene, 1,1-dimethyl-1,2-ethylene, 1-hydroxy-methyl-1,2-ethylene, 2-hydroxy-1,3-propylene, 1,3-propylene, 1,4-butylene, 1,5-pentylene, 2-methyl-1,3-propylene, 2-ethyl-1,3-propylene, 2,2-dimethyl-1,3-propylene and 2,2-dimethyl-1,4-butylene; preference is given to 1,4-butylene, 1,5-pentylene and 1,3-propylene; particular preference is given to 1,3-propylene.

Examples of $R^2$ are 1,2-ethylene, 1,2-propylene, 1,1-dimethyl-1,2-ethylene, 1-hydroxy-methyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 1,2-cyclopentylene, 1,3-cyclopentylene, 1,2-cyclohexylene, 1,3-cyclohexylene, ortho-phenylene, 3-oxa-1,5-pentylene, 3,6-dioxa-1,8-octylene and 3,6,8-trioxa-1,8,11-undecylene; preference is given to 1,2-ethylene, 1,2-propylene, 1,3-propylene; particular preference is given to 1,2-ethylene and 1,2-propylene and very particular preference is given to 1,2-ethylene.

Preferred species (C) are N-(2-hydroxyethyl)pyrrolidone, N-(2-hydroxypropyl)-pyrrolidone, N-(2'-(2-hydroxyethoxy)ethyl)pyrrolidone, N-(2-hydroxyethyl)caprolactam, N-(2-hydroxypropyl)caprolactam and N-(2'-(2-hydroxyethoxy)ethyl)caprolactam; preference is given to N-(2-hydroxyethyl)pyrrolidone and N-(2-hydroxypropyl)-pyrrolidone; particular preference is given to N-(2-hydroxyethyl)pyrrolidone.

According to the invention, the esterification of the alcohol (C) with (meth)acrylic acid or preferably the transesterification of the alcohol (C) with at least one, preferably exactly one, (meth)acrylic ester (D) is effected in the presence of at least one heterogeneous inorganic salt (S).

Compounds (D) may be esters of (meth)acrylic acid with a saturated alcohol, preferably saturated $C_1$-$C_{10}$-alkyl esters of (meth)acrylic acid, more preferably saturated $C_1$-$C_4$-alkyl esters of (meth)acrylic acid.

In the context of this document, saturated means compounds without C—C multiple bonds (except of course the C=C double bond in the (meth)acryloyl units).

Examples of compounds (D) are methyl, ethyl, n-butyl, isobutyl, tert-butyl, n-octyl and 2-ethylhexyl (meth) acrylate, 1,2-ethylene glycol di- and mono(meth)acrylate, 1,4-butanediol di- and mono(meth)acrylate, 1,6-hexanediol di- and mono(meth)acrylate, trimethylolpropane tri(meth)acrylate and pentaerythritol tetra(meth)acrylate.

Particular preference is given to methyl, ethyl, n-butyl and 2-ethylhexyl (meth)acrylate, very particular preference to methyl, ethyl and n-butyl (meth)acrylate, in particular to methyl and ethyl (meth)acrylate and especially to methyl (meth)acrylate).

Inorganic salts (S) usable in accordance with the invention are those which have a $pK_B$ value of not more than 7.0, preferably of not more than 6.1 and more preferably of not more than 4.0. At the same time, the $pK_B$ value should not be less than 1.0, preferably not less than 1.5 and more preferably not less than 1.6.

In the context of this document, heterogeneous catalysts are, in accordance with the invention, those which have a solubility in the reaction medium at 25° C. of not more than 1 g/l, preferably of not more than 0.5 g/l and more preferably of not more than 0.25 g/l.

The inorganic salt preferably has at least one anion selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), hydrogensulfate ($HSO_4^-$), hydrogensulfite ($HSO_3^-$) and carboxylate ($R^6$—COO—), where $R^6$ is $C_1$-$C_{18}$-alkyl, or $C_2$-$C_{18}$-alkyl or $C_6$-$C_{12}$-aryl optionally interrupted by one or more oxygen and/or sulfur atoms and/or one or more substituted or unsubstituted imino groups.

Preference is given to carbonate and phosphate.

Phosphate is also understood to mean the condensation products, for example diphosphates, triphosphates and polyphosphates.

The inorganic salt preferably has at least one cation selected from the group consisting of alkali metals, alkaline earth metals, ammonium, cerium, iron, manganese, chromium, molybdenum, cobalt, nickel or zinc.

Preference is given to alkali metals and particular preference to lithium, sodium or potassium.

Particularly preferred inorganic salts are $Li_3PO_4$, $K_3PO_4$, $Na_3PO_4$ and $K_2CO_3$, and also their hydrates; very particular preference is given to $K_2CO_3$ and $K_3PO_4$.

According to the invention, $K_3PO_4$ may be used in anhydrous form, and also as the tri-, hepta- or nonahydrate.

The esterification or transesterification catalyzed by an inorganic salt is effected generally at from 30 to 140° C., preferably at from 30 to 100° C., more preferably at from 40 to 90° C. and most preferably at from 50 to 80° C.

If appropriate, the reaction may be carried out under gentle vacuum of, for example, from 150 hPa to standard pressure, preferably from 200 to 600 hPa and more preferably 200 to 400 hPa when the water released in the esterification or the low-boiling alcohol formed in the transesterification, if appropriate as an azeotrope, is to be distilled off.

The molar ratio between (meth)acrylic acid or (meth) acrylic ester and alcohol (C) in the esterification or transesterification catalyzed by an inorganic salt is generally 1-6:1 mol/mol, preferably 1-5.5:1 mol/mol and more preferably 1-5.0:1 mol/mol.

The reaction time in the esterification or transesterification catalyzed by an inorganic salt is generally from 45 min to 18 hours, preferably from 1.5 hours to 12 hours and more preferably from 2 to 8 hours.

The content of inorganic salts in the reaction medium is generally in the range from about 0.01 to 5 mol %, preferably 0.1-1.8 and more preferably 1-2.5 mol %, based on the sum of the components (C) used.

In the esterification or transesterification, polymerization inhibitors (see below) are necessarily required.

The presence of oxygenous gases (see below) during the reaction catalyzed by an inorganic salt is preferred.

In the esterification or transesterification catalyzed by an inorganic salt, the products are generally obtained with a color number below 500 APHA, preferably below 200 and more preferably below 150 (to DIN ISO 6271).

The reaction can proceed in organic solvents or mixtures thereof, or without addition of solvents. The mixtures are generally substantially anhydrous (i.e. water content below 10, preferably below 5, more preferably below 1 and most preferably below 0.5% by weight). Moreover, the mixtures are substantially free of primary and secondary alcohols, i.e. alcohol content below 10, preferably below 5, more preferably below 1 and most preferably below 0.5% by weight.

Suitable organic solvents are those known for these purposes, for example tertiary monools such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, for example 1,2-dimethoxyethane, diethylene glycol dimethyl ether, polyethylene glycol dimethyl ether 500, $C_1$-$C_4$-alkylene carbonates, especially propylene carbonate, $C_3$-$C_6$-alkyl acetates, especially tert-butyl acetate, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and their mono- or multiphasic mixtures.

In a particularly preferred embodiment of the transesterification, the reaction is carried out in the presence of the (meth)acrylic ester used as the reactant. Very particular preference is given to performance of the reaction in such a way that the product (C), after the reaction has ended, is obtained as an about 10-80% by weight solution in the (meth)acrylic ester used as the reactant, in particular as a from 20 to 50% by weight solution.

The reactants are present in the reaction medium either dissolved, suspended as solids or in emulsion.

The reaction may be effected continuously, for example in a tubular reactor or in a stirred tank battery, or batchwise.

The reaction may be carried out in all reactors suitable for such a reaction. Such reactors are known to those skilled in the art. Preference is given to effecting the reaction in a stirred tank reactor or a fixed bed reactor.

To mix the reaction mixture, any methods may be used. Specific stirrer apparatus is not required. The mixing can be effected, for example, by feeding in a gas, preferably an oxygenous gas (see below). The reaction medium may be mono- or multiphasic and the reactants are dissolved, suspended or emulsified therein. During the reaction, the temperature is adjusted to the desired value and may, if desired, be increased or reduced during the course of the reaction.

The removal of water in the case of an esterification or alcohols which are released from the alkyl (meth)acrylates in a transesterification is effected continuously or stepwise in a manner known per se, for example by reduced pressure, azeotropic removal, stripping, absorption, pervaporation and diffusion, by means of membranes or extraction.

The stripping can be effected, for example, by passing an oxygenous gas, preferably air or an air-nitrogen mixture, through the reaction mixture, if appropriate in addition to a distillation.

Suitable methods for absorption are preferably molecular sieves or zeolites (pore size, for example, in the range of about 3-10 ångström), a removal by distillation or with the aid of suitable semipermeable membranes.

However, it is also possible to feed the removed mixture of alkyl (meth)acrylate and its parent alcohol, which frequently forms an azeotrope, directly into a plant for preparing the alkyl (meth)acrylate, in order to reutilize it there in an esterification with (meth)acrylic acid.

After the reaction has ended, the resulting reaction mixture can be used without further purification or, if required, purified in a further step.

In general, the purification step only removes the heterogeneous catalyst used from the reaction mixture and the reaction product from any organic solvent used.

Removal of the heterogeneous catalyst is effected generally by filtration, electrofiltration, absorption, centrifugation or decantation. The heterogeneous catalyst removed may subsequently be used for further reactions.

The removal from the organic solvent is effected generally by distillation, rectification or, in the case of solid reaction products, by filtration.

However, the purification step preferably removes only the heterogeneous catalyst and any solvent used.

The reaction mixture, purified if appropriate, is preferably subjected to a distillation in which the (meth)acrylate of the N-hydroxyalkylated lactams is separated distillatively from unconverted (meth)acrylic acid or unconverted (meth)acrylic ester (D), and also any by-products formed.

The distillation units are usually rectification columns of customary design with circulation evaporators and condensers. The feed is preferably into the bottom region; the bottom temperature here is, for example, 100-180° C., preferably 110-170° C. and more preferably 125-155° C., the top temperature preferably 140-145° C., and the top pressure 3-20 mbar, preferably from 3 to 5 mbar. It will be appreciated that the person skilled in the art can also determine other temperature and pressure ranges in which the particular (meth)acrylates of the N-hydroxyalkylated lactams can be purified by distillation. What is essential is a separation of the desired product from reactants and by-products under conditions under which the desired product is exposed as far as possible to no degradation reaction.

The distillation unit has generally from 5 to 50 theoretical plates. The distillation units are of a design known per se and have the customary internals. Useful column internals are in principle all common internals, for example trays, packings and/or random packings. Among the trays, preference is given to bubble-cap trays, sieve trays, valve trays, Thorman trays and/or dual-flow trays; among the random packings, preference is given to those comprising rings, helices, saddles, Raschig, Intos or Pall rings, barrel or Intalox saddles, Top-Pak etc., or braids.

The desired product is preferably distilled batchwise, which first removes low boilers from the reaction mixture, usually solvent or unconverted (meth)acrylic acid or (meth)acrylic ester (D). After removal of these low boilers, the distillation temperature is increased and/or the vacuum is reduced, and the desired product is distilled off.

The remaining distillation residue is usually discarded.

Owing to the reaction conditions, the formation of by-products in the reaction is prevented, which can otherwise stem, for example, from chemical catalysts or as a result of undesired free-radical polymerization of the (meth)acrylate used, which can otherwise only be prevented by addition of stabilizers. In the inventive reaction, additional stabilizer can be added to the reaction mixture over and above the storage stabilizer present in any case in the (meth)acrylic compound, for example hydroquinone monomethyl ether, phenothiazine, phenols, for example 2-tert-butyl-4-methylphenol, 6-tert-butyl-2,4-dimethylphenol, aromatic diamines, for example N,N-di-sec-butyl-p-phenylenediamine or N-oxyls such as 4-hydroxy-2,2,6,6-tetramethylpiperidine N-oxyl, 4-oxo-2,2,6,6-tetramethylpiperidine N-oxyl or Uvinul® 4040P from BASF Aktiengesellschaft, for example in amounts of from 10, preferably from 50 to 2000 ppm.

Advantageously, the esterification or transesterification is carried out in the presence of an oxygenous gas, preferably air or air-nitrogen mixtures.

The heterogeneous catalyst used in accordance with the invention can be removed from the end product in an unproblematic manner by virtue of its low solubility. As a result, a simple filtration or decantation generally suffices for workup of the reaction product; complicated washes, neutralizations, distillations and the like for removal of the catalyst can generally be dispensed with.

The catalysts in accordance with the invention exhibit only a low tendency to side reactions. The inorganic salts are usually sufficiently basic to catalyze a transesterification but not too basic to catalyze side reactions, for example Michael reactions, to a relatively high degree.

In addition, the reaction is very selective under the inventive reaction conditions; generally less than 10%, preferably less than 5%, of by-products are found (based on the conversion).

The (meth)acrylates, prepared in accordance with the invention, of N-hydroxyalkylated lactams find use, for example, as monomers or comonomers in the preparation of poly(meth)acrylates and dispersions, for example acrylic dispersions, as reactive diluents, for example as radiation-curable coating compositions or in paints, preferably in exterior paints, and also in dispersions for use in the paper sector.

The examples which follow are intended to illustrate the properties of the invention but without restricting it.

EXAMPLES

In this document, unless stated otherwise, "parts" are understood to mean "parts by weight".

Examples 1 to 4

In a transesterification apparatus (1 1 4-neck flask with Vigreux column and liquid distributor), the transesterification of methyl methacrylate (MMA) with hydroxyethylpyrrolidone (HEP) was carried out at a bath temperature of 100° C. under reduced pressure (approx. 400-700 mbar) over 4-5 hours. This was done by initially charging hydroxyethylpyrrolidone as a liquid, diluting it with methyl methacrylate (molar methyl methacrylate:hydroxyethylpyrrolidone ratio=5.6:1) and then starting the reaction by adding the catalyst. The methanol formed was subsequently removed from the reaction mixture as an azeotrope with methyl methacrylate.

To stabilize methyl methacrylate or methacrylates formed in the course of the reaction, stabilizers (50 ppm of phenothiazine and 500 ppm of hydroquinone monomethyl ether) were added and air was introduced. Various catalysts were tested (use in each case of 0.8 mol % based on hydroxyethylpyrrolidone).

After the end of the reaction time, the remaining liquid phase was analyzed by gas chromatography (amounts in area percent):

TABLE 1

Reaction of hydroxyethylpyrrolidone with various catalysts

| Example | Catalyst | Methanol [area %] | Methyl methacrylate [area %] | Hydroxyethyl-pyrrolidone [area %] | Product of value [area %] |
| --- | --- | --- | --- | --- | --- |
| 1 | $K_3PO_4$ | 0.1 | 25.3 | 5.2 | 66.2 |
| 2 | $K_2CO_3$ | 0.1 | 2.6 | 16.9 | 78.8 |
| 3 (comparison) | $NaOCH_3$ | 0.1 | 42.2 | 13.9 | 42.4 |
| 4 (comparison) | $Ti(OiPr)_4$ | — | 21.7 | 75.1 | 2.6 |

It can be seen that the inventive catalysts afforded a distinctly higher fraction of product of value by a transesterification than with sodium methoxide or titanium tetraisopropoxide.

Example 5

A 750 ml reactor with Oldershaw column and liquid distributor was initially charged with 280 mg of hydroquinone monomethyl ether (350 ppm), 600 g (6.0 mol) of methyl methacrylate (MMA) and 194 g (1.5 mol) of N-hydroxyethylpyrrolidone, which were stirred at a stirrer speed (anchor stirrer) of 400 rpm and an air supply of 1.5 l/h. Subsequently, 6.37 g (30 mmol; 2.0 mol % based on N-hydroxyethylpyrrolidone) of anhydrous potassium phosphate were added, the vacuum was established (300 mbar) and the suspension was heated (the jacket temperature was adjusted to 120° C. by means of thermostat control). After approx. 20 minutes, the suspension began to boil (t=0 min). During the reaction, distillate was removed continuously (reflux:efflux ratio was 25:1) and the temperature in the bottom rose from approx. 63° C. to 79° C. After 300 min, the reaction was ended and the vacuum was removed. The suspension was cooled and then filtered through a pressure suction filter (30 ml of methyl methacrylate were added to flush the residue). 492 g of crude product were obtained, which were admixed with 200 ppm of N,N-di-sec-butyl-p-phenylenediamine (98 mg) and were distilled with a supply of air. This first removed the excess methyl methacrylate and then afforded the product of value (130° C., 1.3 mbar). 273 g (92%) of N-hydroxyethylpyrrolidone methacrylate (N-(2-(methacryloyl)ethyl)pyrrolidone) were obtained in high purity (GC analysis: 99.6%). The color number was 50 (APHA color number).

Thus, a higher yield is obtained in the transesterification with an inventive catalyst than in the case of the acidic esterification according to WO 03/6568.

Example 6

The apparatus described in example 5 was initially charged with 280 mg of hydroquinone monomethyl ether (350 ppm), 600 g (6.0 mol) of methyl methacrylate (MMA) and 194 g (1.5 mol) of N-hydroxyethylpyrrolidone, which were stirred. Subsequently, 4.15 g (30 mmol; 2.0 mol % based on N-hydroxyethylpyrrolidone) of potassium carbonate were added, the vacuum was established (300 mbar) and the suspension was heated (the jacket temperature was adjusted to 120° C. by means of thermostat control). After approx. 20 minutes, the suspension began to boil (t=0 min). During the reaction, distillate was removed continuously and the temperature in the bottom rose from approx. 63° C. to 79° C. After 300 min, the reaction was ended and the vacuum was removed. The suspension was cooled and then filtered through a pressure suction filter (30 ml of MMA were added to flush the residue).

438 g of crude product were obtained. The excess MMA was first removed. Then, 400 ppm of N,N-di-sec-butyl-p-phenylenediamine (106 mg) were added to the crude product freed of MMA and distilled with supply of air. The product of value was obtained (147° C., 3.6 mbar). 238 g (81%) of N-hydroxyethylpyrrolidone methacrylate (N-(2-(methacryloyl)ethyl)pyrrolidone) were obtained in high purity (GC analysis: 99.7%). The color number was approx. 60 (APHA color number).

Example 7

The apparatus described in example 5 was initially charged with 280 mg of hydroquinone monomethyl ether (350 ppm), 600 g (6.0 mol) of methyl methacrylate and 194 g (1.5 mol) of N-hydroxyethylpyrrolidone (APHA color number=117), which were stirred. Subsequently, 4.15 g (30 mmol; 2.0 mol % based on N-hydroxyethylpyrrolidone) of potassium carbonate were added, the vacuum was established (300 mbar) and the suspension was heated (the jacket temperature was adjusted to 120° C. by means of thermostat control). After approx. 15 minutes, the suspension began to boil (t=0 min). During the reaction, distillate (azeotrope of MMA and methanol) was removed continuously. After 150 min, the temperature in the bottom was adjusted to 60° C. and the excess MMA was removed under reduced pressure. Subsequently, the vacuum was removed, and the suspension was cooled and filtered through a pressure suction filter. 289 g of product (yield=98%) were obtained as a slightly yellowish liquid (APHA color number=121) with the following composition (GC analysis, data in %):

| Product* | HEP** | MMA | By-products*** | Color number (APHA) |
|---|---|---|---|---|
| 96.5 | 0.4 | 1.0 | 2.1 | 121 |

*N-hydroxyethylpyrrolidone methacrylate
**N-hydroxyethylpyrrolidone
***sum of by-products The product was analyzed for the content of potassium. A content of <0.001 g/100 g was found.

What is claimed is:

1. A process for preparing a (meth)acrylate of a N-hydroxyalkylated lactam, in which a cyclic N-hydroxyalkylated lactam (C)

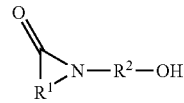

wherein:
R$^1$ is a C$_1$-C$_5$-alkylene group, or a C$_2$-C$_{20}$-alkylene group interrupted by at least one of an oxygen atom, a sulfur atom, a substituted imino group, an unsubstituted imino group, a cycloalkyl group, —(CO)—, —O(CO)O—, —(NH)(CO)O—, —O(CO)(NH)—, —O(CO)— and —(CO)O—, which may be further substituted by at least one of an aryl group, an alkyl group, an aryloxy group, an alkyloxy group, a heteroatom and a heterocycle,
with the proviso that R$^1$ must not have any atom other than a carbon atom directly adjacent to the lactam carbonyl group,
R$^2$ is a C$_1$-C$_{20}$-alkylene group, a C$_5$-C$_{12}$-cycloalkylene a C$_6$-C$_{12}$-arylene group, or a C$_2$-C$_{20}$-alkylene group interrupted by at least one of an oxygen atom, a sulfur atom, a substituted imino group, an unsubstituted imino group, a cycloalkyl group, —(CO)—, —O(CO)O—, —(NH)(CO)O—, —O(CO)(NH)—, —O(CO)— and —(CO)O—, which may be further substituted by at least one of an aryl group, an alkyl group, an aryloxy group, an alkyloxy group, a heteroatom and a heterocycle, or
R$^2$—OH is a group of the formula —[X$_i$]$_k$—H,
k is from 1 to 50 and
X$_i$, is independently selected from the group consisting of —CH$_2$—CH$_2$—O—, —CH$_2$—CH$_2$—N(H)—, —CH$_2$—CH$_2$—CH$_2$—N(H)—, —CH$_2$—CH(NH$_2$)—, —CH$_2$—CH(NHCHO)—, —CH$_2$—CH(CH$_3$)—O—, —CH(CH$_3$)—CH$_2$—O—, —CH$_2$—C(CH$_3$)$_2$—O—, —C(CH$_3$)$_2$—CH$_2$—O—, —CH$_2$—CH$_2$—CH$_2$—O—, —CH$_2$—CH$_2$—CH$_2$—CH$_2$—O—, —CH$_2$—CHVin-O—, —CHVin-CH$_2$—O—, —CH$_2$—CHPh-O— and —CHPh-CH$_2$—O—, and mixtures thereof where Ph is phenyl and Vin is vinyl,
is esterified with (meth)acrylic acid or transesterified with at least one (meth)acrylic ester (D) in the presence of at least one heterogeneous inorganic salt (S).

2. The process according to claim 1, wherein the at least one inorganic salt (S) has a $pK_B$ value of not more than 7.0 and not less than 1.0, and a solubility in the reaction medium at 25° C. of not more than 1 g/l.

3. The process according to claim 1, wherein the inorganic salt has at least one anion selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), hydrogensulfate ($HSO_4^-$), sulfite ($SO_3^{2-}$), hydrogensulfite ($HSO_3^-$) and carboxylate ($R^6$—$COO^-$), where $R^6$ is a $C_1$-$C_{18}$-alkyl group, a $C_2$-$C_{18}$-alkyl group or a $C_6$-$C_{12}$-aryl group which may be further substituted with at least one of an oxygen atom, a sulfur atom, a substituted imino group and an unsubstituted imino group.

4. The process according to claim 1, wherein the inorganic salt has at least one cation selected from the group consisting of an alkali metal, alkaline earth metal, ammonium, cerium, iron, manganese, chromium, molybdenum, cobalt, nickel and zinc.

5. The process according to claim 1, wherein the inorganic salt is selected from the group consisting of $Li_3PO_4$, $K_3PO_4$, $Na_3PO_4$ $K_2CO_3$, and hydrates thereof.

6. The process according to claim 1, wherein $R^2$ is selected from the group consisting of 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene 2,2-dimethyl-1,4-butylene, 1,2-cyclopentylene, 1,3-cyclopentylene, 1,2-cyclohexylene, 1,3-cyclohexylene, ortho-phenylene, 3-oxa-1,5-pentylene, 3,6-dioxa-1,8-octylene and 3,6,8-trioxa-1,8,11-undecylene.

7. The process according to claim 1, wherein $R^1$ is selected from the group consisting of 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,5-pentylene, 2-methyl-1,3-propylene, 2-ethyl-1,3-propylene, 2,2-dimethyl-1,3-propylene and 2,2-dimethyl-1,4-butylene.

8. The process according to claim 1, wherein (C) is selected from the group consisting of N-(2-hydroxyethyl)-pyrrolidone, N-(2-hydroxypropyl)-pyrrolidone, N-(2'-(2-hydroxyethoxy)ethyl)pyrrolidone, N-(2-hydroxyethyl)-caprolactam, N-(2-hydroxypropyl)caprolactam and N-(2'-(2-hydroxyethoxy)ethyl)-caprolactam.

9. A process for making a (meth)acrylate of an N-hydroxy-alkylated lactam, comprising:
at least one of
(I) esterifying a cyclic N-hydroxyalkylated lactam of formula (C) with a (meth)acrylic acid in the presence of at least one heterogeneous inorganic salt; and
(II) transesterifying the cyclic N-hydroxyalkylated lactam of formula (C) with at least one (meth)acrylic ester in the presence of the heterogeneous inorganic salt;

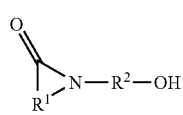

(C)

wherein $R^1$ is a $C_1$-$C_5$-alkylene group, or a $C_2$-$C_{20}$-alkylene group interrupted by at least one of an oxygen atom, a sulfur atom, a substituted imino group, an unsubstituted imino group, a cycloalkyl group, —(CO)—, —O(CO)O—, —(NH)(CO)O—, —O(CO)(NH)—, —O(CO)— and —(CO)O— which may be further substituted by at least one of an aryl group, an alkyl group, an aryloxy group, an alkyloxy group, a heteroatom and a heterocycle, with the proviso that $R^1$ must not have any atom other than a carbon atom directly adjacent to the lactam carbonyl group, $R^2$ is a $C_1$-$C_{20}$-alkylene group, a $C_5$-$C_{12}$-cycloalkylene group, a $C_6$-$C_{12}$-arylene group, or a $C_2$-$C_{20}$-alkylene group interrupted by at least one of an oxygen atom, a sulfur atom, a substituted imino group, an unsubstituted imino group, a cycloalkyl group, —(CO)—, —O(CO)O—, —(NH)(CO)O—, —O(CO)(NH)—, —O(CO)— and —(CO)O— which may be further substituted by at least one of an aryl group, an alkyl group, an aryloxy group, an alkyloxy group, a heteroatom and a heterocycle, or $R^2$—OH is a group of the formula —$[X_i]_k$—H, k is from 1 to 50 and $X_i$ is independently selected from the group consisting of —$CH_2$—$CH_2$—O—, —$CH_2$—$CH_2$—N(H)—, —$CH_2$—$CH_2$—$CH_2$—N(H)—, —$CH_2$—$CH(NH_2)$—, —$CH_2$—$CH(NHCHO)$—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh-O— and —CHPh-$CH_2$—O—, and mixtures thereof where Ph is phenyl and Vin is vinyl.

10. The process according to claim 9, wherein the at least one inorganic salt (S) has a $pK_B$ value of not more than 7.0 and not less than 1.0, and a solubility in the reaction medium at 25° C. of not more than 1 g/l.

11. The process according to claim 9, wherein the inorganic salt has at least one anion selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), hydrogensulfate ($HSO_4^-$), sulfite ($SO_3^{2-}$), hydrogensulfite ($HSO_3^-$) and carboxylate ($R^6$—$COO^-$), where $R^6$ is a $C_1$-$C_{18}$-alkyl group, a $C_2$-$C_{18}$-alkyl group or a $C_6$-$C_{12}$-aryl group which may be substituted with at least one of an oxygen atom, a sulfur atom, a substituted imino group and an unsubstituted imino group.

12. The process according to claim 9, wherein the inorganic salt has at least one cation selected from the group consisting of an alkali metal, an alkaline earth metal, ammonium, cerium, iron, manganese, chromium, molybdenum, cobalt, nickel and zinc.

13. The process according to claim 9, wherein the inorganic salt is selected from the group consisting of $Li_3PO_4$, $K_3PO_4$, $Na_3PO_4$ $K_2CO_3$, and hydrates thereof.

14. The process according to claim 9, wherein $R^2$ is selected from the group consisting of 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 1,2-cyclopentylene, 1,3-cyclopentylene, 1,2-cyclohexylene, 1,3-cyclohexylene, ortho-phenylene, 3-oxa-1,5-pentylene, 3,6-dioxa-1,8-octylene and 3,6,8-trioxa-1,8,11-undecylene.

15. The process according to claim 9, wherein $R^1$ is selected from the group consisting of 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,5-pentylene, 2-methyl-1,3-propylene, 2-ethyl-1,3-propylene, 2,2-dimethyl-1,3-propylene and 2,2-dimethyl-1,4-butylene.

16. The process according to claim 9, wherein (C) is selected from the group consisting of N-(2-hydroxyethyl)-pyrrolidone, N-(2-hydroxypropyl)-pyrrolidone, N-(2'-(2-hydroxyethoxy)ethyl)pyrrolidone, N-(2-hydroxyethyl)-caprolactam, N-(2-hydroxypropyl)caprolactam and N-(2'-(2-hydroxyethoxy)ethyl)-caprolactam.

* * * * *